(12) United States Patent
Wendelbo et al.

(10) Patent No.: US 6,677,162 B1
(45) Date of Patent: Jan. 13, 2004

(54) PROCESS OF PARALLEL SAMPLE PREPARATION

(75) Inventors: Rune Wendelbo, Oslo (NO); Duncan E. Akporiaye, Oslo (NO); Ivar M. Dahl, Oslo (NO); Arne Karlsson, Oslo (NO); Gregory J. Lewis, Mount Prospect, IL (US); David S. Bem, Arlington Heights, IL (US); Andrzej Z. Ringwelski, Marengo, IL (US); Richard C. Murray, Jr., Palatine, IL (US); Cheryl M. Bratu, Park Ridge, IL (US)

(73) Assignee: UOP LLC, Des Plaines, IL (US)

( * ) Notice: Subject to any disclaimer, the term of this patent is extended or adjusted under 35 U.S.C. 154(b) by 258 days.

(21) Appl. No.: 09/884,508

(22) Filed: Jun. 15, 2001

Related U.S. Application Data

(60) Provisional application No. 60/218,777, filed on Jul. 18, 2000.

(51) Int. Cl.[7] .............................. B01L 3/00; G01N 1/00; G01N 23/20; G01N 23/207; C12M 1/34; C12M 3/00; C12M 1/23; B67D 5/64

(52) U.S. Cl. .................... 436/174; 422/102; 422/99; 436/174; 435/288.4; 435/305.1; 435/305.2; 435/305.4; 222/174; 222/168; 378/70; 378/71; 378/75

(58) Field of Search .................. 422/99, 102; 436/174; 435/288.4, 288.5, 305.1, 305.2, 305.4; 378/70, 71, 75; 222/168, 174

(56) References Cited

U.S. PATENT DOCUMENTS

| | | | |
|---|---|---|---|
| 2,317,329 A | 4/1943 | McLachlan, Jr. ............. 250/53 |
| 3,177,360 A | 4/1965 | Hague, Jr. et al. ......... 250/51.5 |
| 3,518,752 A | * | 7/1970 | Lentz ........................ 29/592.1 |
| 3,598,992 A | 8/1971 | Bridge, Jr. ..................... 250/51 |
| 3,925,678 A | 12/1975 | Eberspaecher et al. ..... 250/508 |
| 4,278,883 A | 7/1981 | Hathaway et al. .......... 250/277 |
| 4,299,920 A | * | 11/1981 | Peters ...................... 435/288.4 |
| 4,526,690 A | 7/1985 | Kiovsky et al. ............. 210/235 |
| 4,641,329 A | 2/1987 | Green et al. .................. 378/79 |

(List continued on next page.)

FOREIGN PATENT DOCUMENTS

| | | | | |
|---|---|---|---|---|
| WO | WO 98/55232 | 12/1998 | ............. B01L/3/00 |
| WO | WO 00/36405 | 6/2000 | .......... G01N/23/20 |

OTHER PUBLICATIONS

Klien, J.; Lehmann, C. W.; Schmidt, H.; Majer, W. F. *Angew Chem. Int. Ed.* 1998, 37, 3369–3372.
Choi, K.; Gardner, D.; Hilbrandt, N.; Bein, T. *Angew. Chem. Int. Ed.* 1999, 38, No. 19, 2891–94.

*Primary Examiner*—Jill Warden
*Assistant Examiner*—B. R Gordon
(74) *Attorney, Agent, or Firm*—John G. Tolomei; Frank S. Molinaro; Maryann Maas

(57) ABSTRACT

A process of forming an array of powder samples arranged in predefined locations where all samples have a flat surface in a common plane has been developed. A main support having at least N perforations from a first surface of the main support through a second surface of the main support in predefined locations, where N is the number of samples in the array is provided. The main support is equipped with a flat support temporarily attached to its first surface. All N samples are loaded simultaneously with sample X in perforation X of the main support where X is an integer from 1 to N. A flat surface of each sample where the flat surfaces are a common plane is formed by forcing the samples within the perforations against the flat support. The samples are retained in position within the perforations against the flat support, and are made ready for analysis by exposing the flat surfaces of the samples by removing the flat support. The exposed flat surfaces of the samples are in predefined locations and are all in a common plane. Alternatively, the flat support may be permanently attached to the main support.

39 Claims, 1 Drawing Sheet

U.S. PATENT DOCUMENTS

| | | | |
|---|---|---|---|
| 4,770,593 A | 9/1988 | Anderson | 414/321 |
| 4,895,706 A | 1/1990 | Root et al. | 422/102 |
| 5,002,735 A * | 3/1991 | Alberhasky et al. | 422/99 |
| 5,084,910 A | 1/1992 | Albe et al. | 378/75 |
| 5,096,676 A * | 3/1992 | McPherson et al. | 117/206 |
| 5,127,039 A | 6/1992 | Hesch | 378/79 |
| 5,273,718 A | 12/1993 | Sköld et al. | 422/101 |
| 5,544,218 A | 8/1996 | Turner et al. | 378/208 |
| 5,686,314 A * | 11/1997 | Miyazaki | 436/177 |
| 5,766,556 A * | 6/1998 | DeWitt et al. | 422/131 |
| 5,958,345 A * | 9/1999 | Turner et al. | 422/104 |
| 5,961,926 A * | 10/1999 | Kolb et al. | 422/101 |
| 6,027,873 A | 2/2000 | Schellenberger et al. | 435/4 |
| 6,045,753 A * | 4/2000 | Loewy et al. | 422/57 |
| 6,371,640 B1 | 4/2002 | Hajduk et al. | 378/208 |
| 6,406,670 B1 * | 6/2002 | Earley et al. | 422/99 |
| 2003/0030184 A1 * | 2/2003 | Kim et al. | 264/325 |
| 2003/0044324 A1 * | 3/2003 | Micklash, II et al. | 422/102 |

* cited by examiner

PROCESS OF PARALLEL SAMPLE PREPARATION

CROSS REFERENCE TO RELATED APPLICATION

This application claims the benefit of priority of our Provisional Application No. 60/218,777 filed Jul. 18, 2000.

FIELD OF THE INVENTION

The invention relates to a process and apparatus for the parallel isolation and preparation of multiple samples for powder X-ray diffraction analysis.

BACKGROUND OF THE INVENTION

X-ray powder diffractometry is a commonly used analytical technique for identifying the structure of a material. Fundamentally, the procedure involves directing a small beam of monochromatic X-rays into a polycrystalline sample and then recording the resultant pattern of diffracted X-rays as diffraction signal peaks on film or using a detector. Since different substances produce unique diffraction patterns due to their atomic arrangement, this technique serves as a "fingerprint" for identification of both known and unknown materials.

General sample preparation for X-ray powder diffractometry involves placing a powder sample into a sample holder which is then inserted into the X-ray powder diffractometer. The design of the sample holder is important for both ease of use and for obtaining the best analytical results. For example, collection of the desired data is enhanced if the sample holder is constructed of material which does not produce strong background signal intensity which may alter or conceal small peaks caused by the sample. If the construction material of the sample holder does produce large diffraction peaks, it is preferred that the large diffraction peaks not be in the vicinity of the diffraction peaks of interest from the sample.

Traditionally, a sample holder for X-ray powder diffractometry would contain a single sample for analysis, with sample changers being used to analyze multiple samples in sequence. However, with the growth of combinatorial approaches to the synthesis of new materials, a need has arisen for handling and preparing arrays of samples for analysis. The most efficient techniques are those that manipulate entire arrays of samples in parallel as opposed to manipulating samples individually, i.e., one at a time. One such approach is documented in Choi, Kwangwook; Gardner, David; Hilbrandt, Nicole, Bein, Thomas, *Angew. Chem. Int. Ed.* 1999, 38, No. 19, 2891–94 where products from hydrothermal synthesis are washed and isolated as an array using a custom-designed centrifuge apparatus and the samples are collected on filter paper and transferred to a sample holder for X-ray analysis. The custom-designed centrifuge apparatus consisted of two different filter papers, glass microfibre and normal filter paper, a PVC main support with a matching hold pattern, a filtrate reservoir and a PVC cylinder. Two pieces of filter paper were placed between the multiclave hydrothermal synthesis vessel and the PVC main support that was connected to the filtrate reservoir. For washing, the multiclave and the PVC main support were turned upside down, and water was added into the holes of the PVC main support and then forced into the multiclave by centrifugation. The steps were repeated several times.

Another approach is disclosed in Klein, Jens; Lehmann, Christian W.; Schmidt, Hans-Werner; Maier, Wilhelm F. *Angew. Chem. Int. Ed.* 1998 37, No. 24, 3369–72 where the bottom of a multiclave synthesis vessel is a silicon wafer. Upon completion of the reaction in an autoclave and cooling, reaction solution was removed from the solids using small porous rods with the solids remaining on the surface of the silicon wafer. The product was washed several times directly in the multiclave synthesis vessel and heated to remove the moisture. The silicon wafer with dried-on crystals was removed and calcined and the products sintered onto the silicon wafer. The silicon wafer was mounted in the X-ray diffractometer and the beam was focussed at the location of each individual spot of sample.

The invention disclosed herein, however, provides a process and apparatus for preparing an array of samples where each sample has a flat surface at a predefined location and where the flat surfaces are in a common plane. The sample preparation of the present invention allows for the sample holder containing the array of samples to be positioned within an X-ray powder diffractometer in a matter of seconds and the array of samples to be analyzed in a very efficient manner.

SUMMARY OF THE INVENTION

One purpose of the present invention is to provide a process of forming an array of powder samples arranged in predefined locations where all samples have a flat surface in a common plane. This is accomplished by first providing a main support having at least N perforations from a first surface of the main support through a second surface of the main support in predefined locations, where N is the number of samples in the array. The main support is equipped with a flat support temporarily attached to its first surface. Then all N samples are loaded simultaneously with sample X in perforation X of the main support where X is an integer from 1 to N. A flat surface of each sample where the flat surfaces are a common plane is formed by forcing the samples within the perforations against the flat support. The samples are retained in position within the perforations against the flat support and are made ready for analysis by exposing the flat surfaces of the samples by removing the flat support. The exposed flat surfaces of the samples are in predefined locations and are all in a common plane.

Another purpose of the invention is to provide another process of forming an array of powder samples arranged in predefined locations where all samples have a flat surface in a common plane by first providing a main support having at least N perforations from a first surface of the main support to a second surface of the main support in predefined locations, where N is the number of samples in the array. The process next involves providing a flat support attached to the first surface of the main support where the flat support is typically from about 1 to about 10 microns thick and is constructed of material which preferably has no more than a minimal X-ray powder diffraction pattern at the angles of interest. The array of samples is simultaneously loaded into the main support with sample X in perforation X of the main support where X is an integer from 1 to N. The flat surface of each sample is formed where the flat surfaces are in a common plane by forcing the samples within the perforations against the flat support. Again, the flat surfaces are formed in predefined locations and are all in a common plane.

BRIEF DESCRIPTION OF THE DRAWINGS

In FIG. 1, the perforations in the main support are of the same diameter throughout the main support.

In FIG. 2, the perforations in the main support have a smaller diameter at the intersection with the first surface of the main support than at the intersection with the second surface of the main support.

In FIG. 3, a film is attached to the first surface of the main support before the flat support is attached.

In FIG. 4, a piston is used as a retaining means and is positioned within the perforations of the main support.

DETAILED DESCRIPTION OF THE INVENTION

Figure 1:
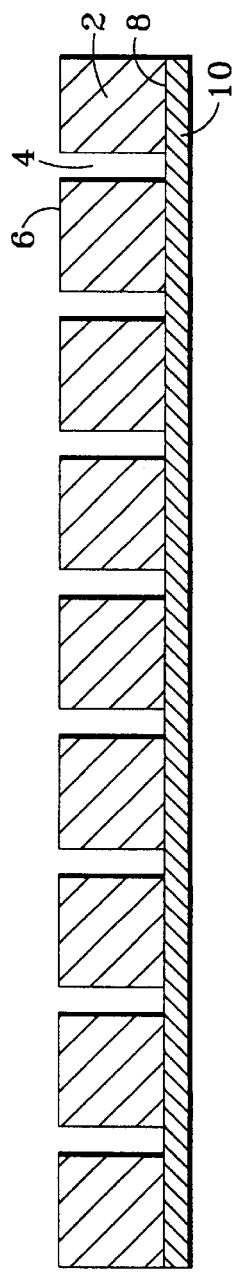
FIG. 1 is a sectional view of one embodiment of the sample holder of the invention.

The present invention is a process for the parallel sample preparation of an array of samples which will typically be employed prior to performing sample analyses. The process was developed for use in preparing an array of samples for analysis by X-ray powder diffractometry, but the process may be used in preparation for analysis for any analytical technique that would benefit from having the array of samples in predefined locations and all having a flat surface in a common plane. For example, other analyses that may benefit from the sample preparation of the present invention include scanning electron microscopy, X-ray fluorescence, X-ray absorption, near edge spectroscopy, diffuse reflectance infrared Fourier transform spectroscopy (DRIFTS), diffuse reflectance ultraviolet-visible spectroscopy, Raman spectroscopy, and photoacoustic infrared spectroscopy. For ease of understanding, the discussion below will focus on the situation where the array of samples is prepared for the analytical technique of X-ray powder diffractometry.

Several criteria are important when preparing an array of samples for X-ray powder diffractometry. First, it is important that the flat surfaces of the samples in the array are formed in predefined locations. Assigning predefined locations allows for the proper repeatable positioning of each sample within the X-ray powder diffractometer. Assigned, predefined sample locations also provide enhanced efficiency for the analysis of large numbers of samples by providing the opportunity for standard sample positioning. For example, in X-ray powder diffractometry, it is difficult and time consuming to sequentially focus the X-ray beam on randomly positioned spots on a silicon wafer. Sequential focusing at random positions may be successful; see Klein, Jens; Lehmann, Christian W.; Schmidt, Hans-Werner; Maier, Wilhelm F. *Angew. Chem. Int. Ed.* 1998 37, No. 24, 3369–72, but the present invention provides superior efficiency through the formation of the flat surfaces in predefined locations. Each of the samples is positioned in "diffracting position" which is at the center of the diffraction circle. The X-ray tube and detector are generally fixed on arms that move them around the diffraction circles and are generally not readjusted or routinely aligned. The predefined locations of the present invention provide efficiency improvement in that the sample holder may be moved among predefined stop positions in an automated fashion thereby eliminating the need for the samples to be individually aligned for each sample analysis. Second, it is important that the surface of the sample that is exposed to the X-ray beam is flat. Unless the surface of the sample is flat, the detected diffracted X-rays will not give accurate results since diffraction geometry will not be aligned.

Third, it is important that the flat surfaces of the samples exposed to the X-ray beam are all in a common plane. In the present invention, the sample holder containing the array of samples may be mounted into the X-ray. powder diffractometer as a unit, and the X-ray beam must be able to reach each sample for analysis, even when the X-ray beam is operating at low angles. To illustrate the importance of having the flat surfaces of the samples all in a common plane, take the situation of an array formed by isolated samples on a filter paper and specifically two adjacent samples in the array, Sample A and Sample B. Suppose the quantity of Sample A is high and thus forms a deposit on the filter paper that has a height, H, while the quantity of Sample B is lower and thus forms a deposit on the filter paper that has a height, L. Height H is greater than height L relative to the filter paper surface. When analyzing Sample B, the X-ray beam at times may actually be blocked by height H of sample A and some of the X-ray diffraction detected would be due to the X-ray beam impinging on Sample A and not on the intended Sample B. The resulting data would not be unique to a single sample, but confounded among several samples. The problem is magnified when the X-ray beam is incident at low angles where even relatively small differences in the height of the adjacent samples in the array may cause such interferences.

The process of the present invention achieves these three criteria for a plurality of samples while at the same time increasing efficiency. The process begins with providing the equipment used. Several different types of equipment may be used to accomplish the goals of the process and the preferred embodiments are disclosed here. In a first embodiment, a first component of the equipment is a main support having at least N perforations from a first surface of the main support to a second surface of the main support in predefined locations, where N is the number of samples in the array. See FIG. 1 where the main support is 2 and the N perforations are 4. One example of a suitable main support is a block. The main support may be constructed of material such as Teflon™, polycarbonate, polystyrene, polypropylene, or polyethylene. It is preferred that the main support be constructed of material that 1) does not have a strong X-ray diffraction pattern in the region of interest 2) is lightweight, 3) is inexpensive, 4) is capable of being mass produced; and 5) has durable flat surfaces that do not deform.

Perforations from a first surface 6 of FIG. 1 of the main support to a second surface, 8 of FIG. 1, of the main support provide the predetermined region for each of the samples in the array (discussed in greater detail below). It is preferred that there are at least as many perforations in the main support as there are samples in the array. The perforations in the main support are preferably located in a set basic pattern that is maintained from main support to main support within a particular sample format. The sample format may vary, however, such as the overall number of perforations, i.e., 24, 48, 96 perforations, or the sizes of the perforations. Maintaining a standard basic pattern configuration among different main supports allows for known reproducible locations of samples. Analytical instrumentation may then be configured and programmed to operate with the standard basic pattern of samples. It may be preferred to match the perforation pattern of the main support with a pattern from another unit of equipment such as a set of synthesis reactors or cells, or a wash plate. Matching patterns allow for the simultaneous transfer of sample arrays, which is discussed in greater detail below. The shapes of the perforations are not critical, any may be circular, square, rectangular, or any shape that is capable of being manufactured as a perforation in a main support, but certain shapes do have advantages.

Figure 2:
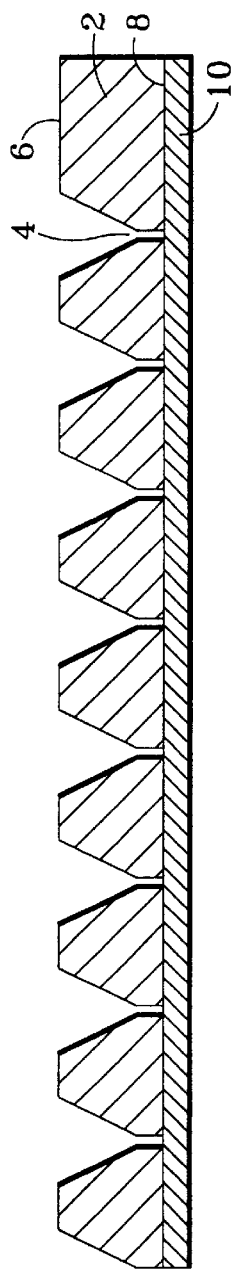
FIG. 2 is a sectional view of another embodiment of the sample holder of the invention.

For example, cylindrical perforations are preferred due to their ease of fabrication. In situations where the quantity of sample is limited, perforations having a reduced cross-section at one surface of the main support are preferred in order to form the required flat surface of sample while using only limited quantities of sample. FIG. 2 shows perforations 4 where the diameter of perforations 4 are greater at the intersection with surface 6 of main support 2 than at surface 8 of main support 2. Using the apparatus shown in FIG. 2 would allow for the flat surfaces of the array of samples to be formed in the same plane with reduced sample volumes.

Adjacent one preferably flat surface of the main support which contains the perforation openings is a flat support, 10 of FIGS. 1 and 2. The flat support may be permanently or temporarily attached to the main support. Depending upon the embodiment of the sample process being employed, the flat support may be constructed of material that allows for transmission of X-rays through the flat surface. It is preferred that the diffraction of X-rays from the flat surface does not yield an X-ray powder diffraction pattern with high noise or peaks at the angles of interest for the samples in the array. Examples of suitable materials include polycarbonate, polyethylene, polypropylene, and lithium borate. When the flat support is made of a material suitable for the transmission of X-rays, it is also preferred that the flat support have a thickness of from about 0.01 micron to about 100 microns, with a more preferred thickness ranging from about 1 micron to about 100 microns and a most preferred thickness ranging from about 1 micron to about 10 microns. When the flat support is only temporarily attached to the main support, the flat support may be constructed of materials that would interfere with the transmission of X-rays or that would result in high noise or interfering peaks, and the flat support is not limited in its thickness. In some embodiments of the process of the invention, the flat surface may be porous, or fluid permeable, with preferred pore sizes ranging from about 0.01 to about 100 microns, and most preferred pore sizes ranging from about 0.1 to about 1 micron. A preferred support is polyester or polycarbonate nucleo-pore filters. The flat support may be attached to the main support by a variety of means including adhesion and pressure seals.

Figure 3:
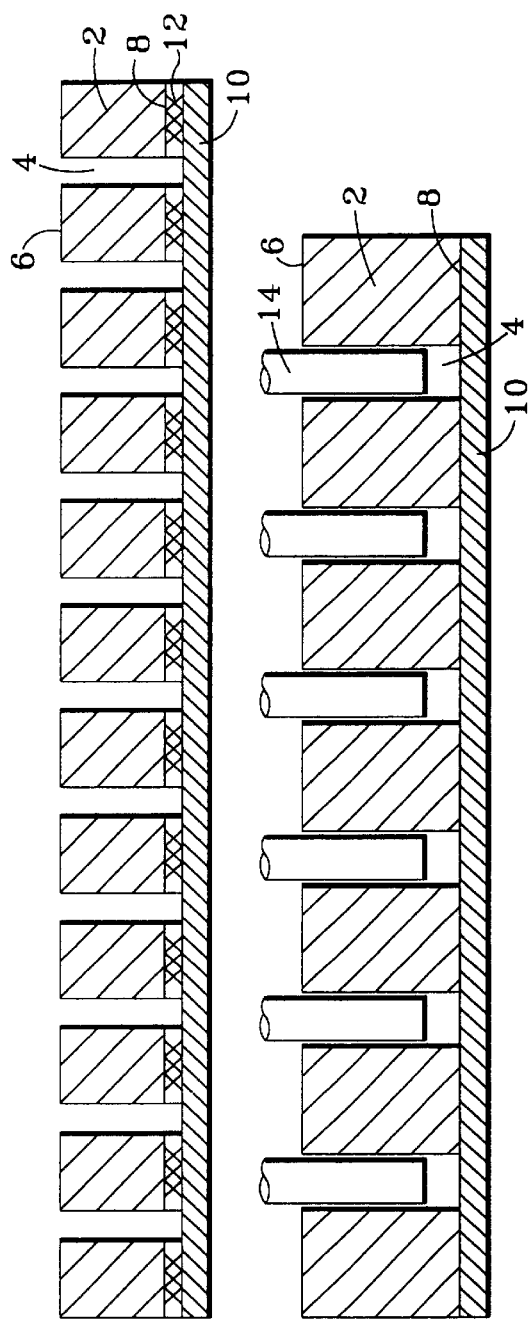
FIG. 3 is a sectional view of yet another embodiment of the sample holder of the invention.

It is most preferred that the X-ray diffraction pattern be free of noise or peaks attributable to the equipment used in holding the array of samples. While the preferred materials of construction for the main support listed above minimize interference, interference may be further eliminated by incorporating an additional layer of material over the main support. In one specific embodiment of the invention, the additional layer of material may be a film or foil of material; see FIG. 3. Film 12 covers only main support 2 and has holes corresponding to perforations 4 in main support 2. It is preferred that the film used have little or no detectable interference in the regions of interest for the particular analytical technique selected. In the case of X-ray powder diffraction, it is preferred that the film be silver film, gold film, aluminum film, nickel film, copper film or zinc film. For other analytical techniques, the film may be a different suitable material. When both the flat support, described above, and the film are used with a single main support, it is preferred that the film is attached to the main support, and then the flat support is attached over the film as shown in FIG. 3. In another embodiment of the invention, a layer of material to eliminate interference may be deposited over the surface of the main support. For example, zinc, copper, nickel, gold, or silver may be deposited over the surface of the main support to prevent interference in the X-ray powder diffraction measurements. For ease of manufacture, a first material may be deposited with a second material being deposited over the first material. For example, for certain support materials, it is preferred to deposit zinc on the main support before depositing, for example, copper or nickel. General deposition techniques may be used to deposit the material and suitable techniques include metal spray (preferred), vapor deposition, metal organic chemical vapor deposition (MOCVD), and sputtering.

The process of the invention next requires the samples to be loaded into the perforations of the main support with each sample being loaded into an individual perforation. The samples may be loaded as dry powder, or the solid particles of the sample may be in a mixture with liquid. For example, the samples may be a product precipitate in a liquid reaction mixture, or the samples may be solid particles in a wash solution. It is preferred that the multiple samples be loaded into the respective perforations simultaneously.

The flat surface of the sample is formed by forcing the samples in the perforations against the flat support. If the samples are a mixture of solid particles and a liquid, forcing the solid sample against the flat support may be accomplished by evaporating, drying, decanting, centrifuging, pipetting, freeze-drying, or adding sponging adsorbents. If the flat support is porous or fluid permeable, the liquid may be removed by centrifugation, gravity filtration, vacuum or suction filtration, or adsorbent filtration thus removing some or all of the liquid from the perforation. It must be emphasized that the term "forcing" as used herein is not limited to manually forcing the sample against the flat surface. The forcing of the samples may be accomplished by mere gravity or the removal of liquid. The sample is considered positioned correctly if it is positioned against the flat support to form a flat surface.

In one embodiment of the invention, the samples are now ready for analysis by X-ray powder diffraction. The flat surface would remain attached to the main support and would preferably be constructed of material providing suitable transmission of the X-rays through the material, i.e., allowing a detectable quantity of X-rays to transmit through the flat surface, without resulting in excessive noise, or large, poorly defined peaks at the angles of interest. It is possible for the flat surface to be constructed out of material that results in peaks at the angles of interest provided that the pattern is well defined and known to the operator. In that situation, the pattern from the flat support may be easily subtracted out of the patterns of the samples. The X-rays would be directed toward the flat surface and the incident X-rays are transmitted through the flat surface to impinge on the sample. The diffracted X-rays are then transmitted back through the flat surface for detection. The X-ray powder diffraction pattern may be detected in any manner commonly known in the art. X-ray powder diffraction techniques are well known in the art and will not be discussed in detail here.

Figure 4:
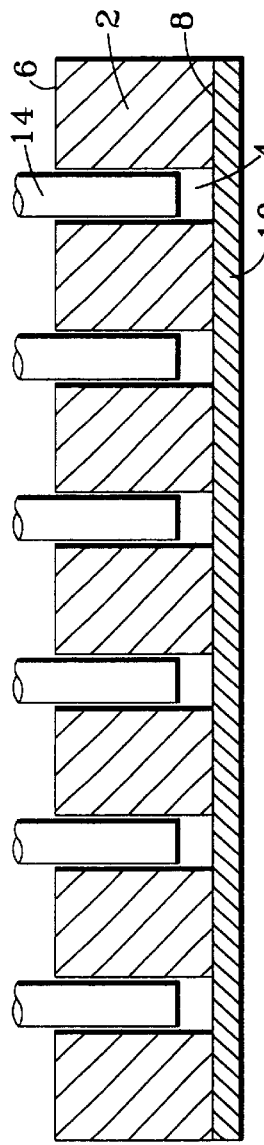
FIG. 4 is a sectional view of still another embodiment of the sample holder of the invention.

Depending upon the X-ray diffractometer and its configuration, the sample holder may be mounted in the instrument so that gravity holds the samples packed against the flat surface of the sample holder. If the sample holder is to be inverted, or placed at various angles, it is preferred to use retaining means within the perforations to retain the sample against the flat surface. The retaining means may be a mechanical device such as a piston, or may be retaining material that is placed in the perforation. FIG. 4 illustrates a mechanical device as a retaining means. In FIG. 4, pistons 14 are positioned within perforations 4 of main support 2. Various retaining materials may be employed with the preferred being amorphous solids. Suitable examples include starch, wax, foil, cross-linked resins, and amorphous metal oxides such as silica, aluminosilicate or aluminophosphate. Preferred materials should not alter the sample, should be effective in retaining the sample in place, and should not contribute to the X-ray powder diffraction pattern In another embodiment of the invention, the flat surfaces of the samples are exposed by removing the flat support that is temporarily attached to the main support. Of course, in this embodiment, before the flat support is removed, the samples are retained in the correct position using the retaining means as described above, i.e., using a mechanical device or by loading additional material, or retaining material, in the perforations. The additional material may be any of those discussed above in the previous embodiment. In this embodiment, it is preferred that the sample holder be placed in the instrument in a manner that allows gravity to aid in retaining the samples in position within the perforations. The term "sample holder" as used herein is meant to encompass all embodiments of the apparatus discussed herein. In some references the sample holder will comprise both the main support and the flat surface, while in other references the sample holder will comprise the main support after the flat surface has been removed and in other references the sample holder will comprise the main support with a film attached to prevent analytical interference from the material of the main support.

The present invention may add great benefit to a combinatorial process for synthesizing materials. In combinatorial synthesis processes, a plurality of materials may be synthesized simultaneously in a parallel set of reactors. Using the present invention, the set of samples may be transferred to the sample holder, washed and ground if necessary, and prepared for X-ray powder diffraction analysis, all in parallel. Specifically, the array of newly synthesized materials may be transferred to the sample holder simultaneously, in parallel, for example, by locating the perforations in the sample holder in a pattern that corresponds to the pattern of the set of reactors, such as a multiautoclave, and inverting the sample holder over the reactors. The set of reactors and the sample holder are temporarily sealed, and the combined equipment is rotated one hundred and eighty degrees so that gravity operates to transfer the material from each of the reactors into a corresponding perforation of the sample holder. After rotation, the sample holder will be on the bottom and the set of reactors will be inverted over the sample holder. If necessary, the reactors may be rinsed with the rinsings being transferred to the sample holder in the same, or any other, manner. The temporary seal may be accomplished by using, for example, a mat, preferably a rubber mat, with perforations that match the patterns of the perforations of the set of reactors and the sample holder. The rubber mat is preferably equipped on each side with formed, raised lips at the perforations that fit snugly into the opening of the reactors and the perforations of the sample holder, ensuring reactor to perforation transfer. The seal may be enhanced by applying pressure. It is contemplated that both the synthesis reactors and the main support and flat surface of the present invention may be equipped with perforations through which bolts may be used to apply pressure and form a seal for the transfer of the sample from the reactors to the perforations of the present invention.

If necessary, the materials transferred into the sample holder may be washed and ground in parallel. Grinding tools such as stainless steel or Teflon™ coated balls may be added to each of the perforations containing the samples. Optionally, a wash fluid may be added to each of the perforations. Water is a preferred wash fluid. The sample holders may then be agitated, manually or mechanically, so that all of the samples in the array are simultaneously ground and washed. Upon completion of the grinding and washing, the grinding tool is removed, and some or all of any liquid present may be removed.

In some applications, the flat surface of the sample holder is not robust enough to withstand the parallel grinding step. The parallel grinding and optional washing may be performed in a wash plate, with the contents of the wash plate being transferred after grinding and the grinding tool removed to the sample holder. The wash plate may be any apparatus having multiple wells for the multiple samples. It is preferred that the pattern of the wells in the wash plate correspond to the pattern of the perforations in the main support of the sample holder for ease of transfer of material from the wash plate to the sample holder. The array of samples may be transferred in any convenient manner such as those described above in the transfer of the samples from the synthesis reactors to the sample holder. Alternatively, a plate may be used to support the flat surface during the grinding and washing stage.

Various different techniques may be employed to remove the liquid from the solid particles. The liquid may be decanted, may be removed via a porous medium inserted into the perforations, or may be pipetted from the perforations. It is preferred to centrifuge the mixtures in the perforations prior to removing the liquid, and it is most preferred to remove the liquid during centrifugation. As discussed above, the flat surface of the sample holder may be constructed of material that is fluid permeable. Therefore, the sample holder may be loaded into a centrifuge and during centrifugation at least a portion of the liquid is forced through the fluid permeable flat surface of the sample holder thereby being separated from the solid particles. Of course, it is preferred to equip the centrifuge with some adsorbent backing or chamber next to the sample holder to collect liquid. The centrifugation technique is further preferred due to the forcing of the solid particles against the flat surface to form all the flat surface in a common plane. The sample holder may then be removed from the centrifuge and placed into the X-ray powder diffractometer. Optionally, as discussed above, a retaining means, such as a mechanical device or retaining material, may be added to the perforations of the sample holder before placement on the X-ray powder diffractometer.

The sample holder is positioned within the X-ray powder diffractometer so that the X-ray beam is directed toward all of the flat surfaces of the samples all in a common plane. In particular, the sample holder is positioned so that the X-ray beam impinges on the flat surface of a first sample. The X-ray powder diffraction pattern of a first sample is obtained, and the sample holder may then be repositioned so that a second sample is in alignment with the X-ray beam. The X-ray diffraction patterns of all the samples may be obtained in this manner. The predefined locations of the samples in the sample holder allow for the automation X-ray diffraction data collection process.

It is important to note that the sample holder and process for forming an array of powder samples arranged in predefined locations where all samples have a flat surface in a common plane may be used in conjunction with other analytical techniques in addition to X-ray powder diffractometry.

What is claimed is:

1. A method of forming an array of powder samples arranged in predefined locations where all samples have a flat surface in a common plane comprising:

(a) providing a main support having at least N perforations from a first surface of the main support to a second surface of the main support in predefined locations, where N is the number of samples in the array and N is at least two;

(b) providing a flat support temporarily attached to the first surface of the main support;

(c) loading sample X in perforation X of the main support where X is an integer from 1 to N;

(d) forming a flat surface of each sample where the flat surfaces are in a common plane by forcing the samples within the perforations against the flat support;

(e) retaining the samples in position within the perforations using retaining means selected from the group consisting of a mechanical device, retaining material added to the perforations to fill additional volume, or a combination thereof; and (f) exposing the flat surfaces of the samples in the predefined regions where the flat surfaces are all in the common plane by removing the flat support.

2. The method of claim 1 wherein the main support is a block.

3. The method of claim 1 wherein the retaining material is at least one amorphous solid.

4. The method of claim 1 further comprising covering the first surface of the main support with a layer of material prior to temporarily attaching the flat support where the material is selected to minimize any interference of the main support in an analytical analysis of the samples.

5. The method of claim 4 wherein the layer of material is in the form of a film or a deposited layer of material.

6. The method of claim 4 wherein the analytical analysis is X-ray powder diffraction and the layer of material is selected from the group consisting of silver, gold, copper, zinc, nickel, and aluminum.

7. The method of claim 1 wherein the samples X are simultaneously loaded into perforations X of the main support.

8. The method of claim 1 further comprising, after loading the samples in act (c) of claim 1:
 (a) adding a wash solution to each perforation; and
 (b) removing the wash solution from each perforation.

9. The method of claim 1 further comprising mounting the main support in an X-ray powder diffraction instrument so that the X-ray beam is directed at the exposed flat surfaces of the samples.

10. The method of claim 9 further comprising obtaining an X-ray powder diffraction pattern of at least one sample.

11. The method of claim 1 further comprising synthesizing the array of samples in a set of synthesis cells prior to loading the samples as in step (c) of claim 1.

12. The method of claim 11 wherein the loading of the array of samples into the perforations is accomplished by simultaneously transferring the samples from the set of synthesis cells to the perforations of the main support.

13. A method of forming an array of powder samples arranged in predefined locations where all samples have a flat surface in a common plane comprising:
 (a) providing a main support having at least N perforations from a first surface of the main support to a second surface of the main support in predefined locations, where N is the number of samples in the array and N is at least two;
 (b) providing a flat support temporarily attached to the first surface of the main support;
 (c) loading sample X in perforation X of the main support where X is an integer from 1 to N;

(d) adding a grinding tool to each perforation;
 (e) agitating the main support and flat support to simultaneously grind the samples in the perforations;
 (f) removing the grinding tool from each perforation;
 (g) forming a flat surface of each sample where the flat surfaces are in a common plane by forcing the samples within the perforations against the flat support;
 (h) retaining the samples in position within the perforations using retaining means; and
 (i) exposing the flat surfaces of the samples in the predefined regions where the flat surfaces are all in the common plane by removing the flat support.

14. The method of claim 13 further comprising reinforcing the flat support temporarily attached to the first surface of the main support using a plate.

15. A method of forming an array of powder samples arranged in predefined locations where all samples have a flat surface in a common plane comprising:
 (a) providing a main support having at least N perforations from a first surface of the main support to a second surface of the main support in ore defined locations, where N is the number of samples in the array and N is at least two;
 (b) providing a flat support temporarily attached to the first surface of the main support;
 (c) loading sample X in perforation X of the main support where X is an integer from 1 to N;
 (d) forming a flat surface of each sample where the flat surfaces are in a common plane by forcing the samples within the perforations against the flat support using the technique of:
  (i) adding a wash liquid and a grinding tool to each perforation;
  (ii) agitating the main support and flat support to simultaneously wash and grind the samples in the perforations; and
  (iii) removing the wash liquid and grinding tool from each perforation; and
  (iv) wherein said technique also washes and grinds the samples;
 (e) retaining the samples in Position within the perforations using retaining means; and
 (f) exposing the flat surfaces of the samples in the predefined regions where the flat surfaces are all in the common plane by removing the flat support.

16. The method of claim 15 further comprising reinforcing the flat support temporarily attached to the first surface of the main support using a plate.

17. The method of claim 15 wherein the wash liquid is removed by a technique selected from the group consisting of, evaporating, drying, decanting, centrifuging, pipetting, freeze-drying, and adding sponging adsorbents.

18. The method of claim 15 wherein the flat support is fluid permeable and the wash liquid is removed using a technique selected from the group consisting of centrifugation, gravity filtration, vacuum or suction filtration, and adsorbent filtration.

19. A method of forming an array of powder samples arranged in predefined locations where all samples have a flat surface in a common plane comprising:
 (a) providing a main support having at least N perforations from a first surface of the main support to a second surface of the main support in predefined locations, where N is the number of samples in the array and N is at least two;

(b) providing a flat support temporarily attached to the first surface of the main support;

(c) synthesizing the array of samples in a set of synthesis cells;

(d) transferring, simultaneously, the array of samples from the set of synthesis cells to a plurality of wells in a wash plate;

(e) adding a wash liquid to each well;

(f) removing the wash liquid from each well;

(g) loading sample X in perforation X of the main support where X is an integer from 1 to N;

(h) forming a flat surface of each sample where the flat surfaces are iii a common plane by forcing the samples within the perforations against the flat support;

(i) retaining the samples in position within the perforations using retaining means; and (j) exposing the flat surfaces of the samples in the pre-defined regions where the flat surfaces are all in the common plane by removing the flat support.

20. The method of claim 19 further comprising:

(a) adding a grinding tool to each well along with the wash liquid in step (e) of claim 21;

(b) agitating the wash plate to simultaneously wash and grind the samples in the wells; and (c) removing the grinding tool from each well.

21. The method of claim 19 wherein the flat support is fluid permeable.

22. A method of forming an array of powder samples arranged in predefined locations where all samples have a flat surface in a common plane comprising:

(a) providing a main support having at least N perforations from a first surface of the main support to a second surface of the main support in predefined locations, where N is the number of samples in the array and N is at least 2;

(b) providing a flat support attached to the first surface of the main support where said flat support is from about 0.01 to about 10 microns thick and is constructed of material which allows for thin sufficient transmission of X-rays;

(c) loading sample X in perforation X of the main support where X is an integer from 1 to N;

(d) forming a flat surface of each sample where the flat surfaces are in a common plane by forcing the samples within the perforations against the flat support; and (e) retaining the samples in position within the perforations using retaining means selected from the group consisting of a mechanical device, retaining material added to the perforations to fill additional volume, or a combination thereof.

23. The method of claim 22 wherein the retaining material is at least one amorphous solid.

24. The method of claim 22 wherein said flat support is fluid permeable.

25. The method of claim 22 wherein the samples X are simultaneously loaded into perforations X of the main support.

26. The method of claim 22 further comprising covering the first surface of the main support with a layer of material prior to attaching the flat support where the material is selected from the group consisting of silver, gold, copper, zinc, nickel, and aluminum.

27. The method of claim 22 further comprising, after loading the samples in act (c) of claim 22:

(a) adding a wash solution to each perforation; and (b) removing the wash solution from each perforation.

28. The method of claim 22 further comprising, after loading the samples in act (c) of claim 22:

(a) adding a grinding tool to each perforation;

(b) agitating the main support and flat support to simultaneously grind the samples in the perforations; and (c) removing the grinding tool from each perforation.

29. The method of claim 28 further comprising reinforcing the flat support temporarily attached to the first surface of the main support using a plate.

30. The method of claim 22 wherein the forcing of the samples within the perforations of act (d) of claim 22 is accomplished by a technique comprising:

(a) adding a wash liquid and a grinding tool to each perforation;

(b) agitating the main support and flat support to simultaneously wash and grind the samples in the perforations; and (c) removing the wash liquid and grinding tool from each perforation;

wherein said technique also washes and grinds the samples.

31. The method of claim 30 further comprising reinforcing the flat support attached to the first surface of the main support using a plate.

32. The method of claim 30 wherein the wash liquid is removed by a technique selected from the group consisting of, evaporating, drying, decanting, centrifuging, pipetting, freeze-drying, and adding sponging adsorbents.

33. The method of claim 30 wherein the flat support is fluid permeable and the wash liquid is removed using a technique selected from the group consisting of centrifugation, gravity filtration, vacuum or suction filtration, and adsorbent filtration.

34. The method of claim 22 further comprising mounting the main support in an X-ray powder diffraction instrument so that the X-ray beam is directed at the flat surfaces of the samples.

35. The method of claim 34 further comprising obtaining X-ray powder diffraction patterns for at least one sample.

36. The method of claim 22 further comprising synthesizing the array of samples in a set of synthesis cells prior to loading the samples in step (c) of claim 22.

37. The method of claim 36 wherein the loading of the samples into the perforations is accomplished through simultaneously transferring the samples from the set of synthesis cells to the perforations of the main support.

38. The method of claim 36 further comprising:

(a) transferring, simultaneously, the array of samples from the set of synthesis cells to a plurality of wells in a wash plate;

(b) adding a wash liquid to each well; and (c) removing the wash liquid from each well.

39. The method of claim 36 further comprising:

(a) transferring, simultaneously, the array of samples from the set of synthesis cells to a plurality of wells in a wash plate;

(b) adding a wash liquid and a grinding tool to each well;

(c) agitating the wash plate to simultaneously wash and grind the samples in the wells; and (d) removing the wash liquid and grinding tool from each well.

* * * * *